(12) United States Patent
Kim et al.

(10) Patent No.: US 11,851,547 B2
(45) Date of Patent: Dec. 26, 2023

(54) CYCLOHEXANE TRIESTER BASED PLASTICIZER COMPOSITION AND RESIN COMPOSITION COMPRISING THE SAME

(71) Applicant: LG CHEM, LTD., Seoul (KR)

(72) Inventors: Hyun Kyu Kim, Daejeon (KR); Yun Ki Cho, Daejeon (KR); Jeong Ju Moon, Daejeon (KR); Joo Ho Kim, Daejeon (KR); Seok Ho Jeong, Daejeon (KR); Woo Hyuk Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 570 days.

(21) Appl. No.: 17/055,029

(22) PCT Filed: Oct. 29, 2019

(86) PCT No.: PCT/KR2019/014322
§ 371 (c)(1),
(2) Date: Nov. 12, 2020

(87) PCT Pub. No.: WO2020/091361
PCT Pub. Date: May 7, 2020

(65) Prior Publication Data
US 2021/0221976 A1 Jul. 22, 2021

(30) Foreign Application Priority Data
Oct. 29, 2018 (KR) ........................ 10-2018-0129866

(51) Int. Cl.
| | |
|---|---|
| C08K 5/12 | (2006.01) |
| C07C 69/75 | (2006.01) |
| C08K 13/08 | (2006.01) |
| C07C 69/76 | (2006.01) |
| C07C 69/94 | (2006.01) |
| C08K 5/11 | (2006.01) |
| C08K 13/00 | (2006.01) |
| C08K 11/00 | (2006.01) |

(52) U.S. Cl.
CPC ............... *C08K 5/12* (2013.01); *C07C 69/75* (2013.01); *C07C 69/76* (2013.01); *C07C 69/94* (2013.01); *C08K 5/11* (2013.01); *C08K 11/00* (2013.01); *C08K 13/00* (2013.01); *C08K 13/08* (2013.01)

(58) Field of Classification Search
CPC .. C08K 5/12; C08K 5/11; C08K 11/00; C08K 13/00; C08K 13/08; C07C 69/75; C07C 69/76; C07C 69/94
See application file for complete search history.

(56) References Cited

U.S. PATENT DOCUMENTS

| | | | | |
|---|---|---|---|---|
| 10,815,361 B2 * | 10/2020 | Magnusson | ............ | C08K 5/1535 |
| 10,875,981 B2 * | 12/2020 | Woldt | ............ | C08K 5/12 |
| 2002/0019559 A1 | 2/2002 | Brunner et al. | | |
| 2005/0020718 A1 | 1/2005 | Gosse et al. | | |
| 2007/0003583 A1 * | 1/2007 | Storzum | ............... | C11B 9/0034 424/401 |
| 2010/0137486 A1 * | 6/2010 | Bueschken | .............. | C08K 5/12 252/182.28 |
| 2011/0053065 A1 | 3/2011 | Wu et al. | | |
| 2011/0232825 A1 | 9/2011 | Mack et al. | | |
| 2012/0071598 A1 | 3/2012 | Gosse et al. | | |
| 2015/0246867 A1 | 9/2015 | Castiglioni et al. | | |
| 2018/0163018 A1 | 6/2018 | Kim et al. | | |
| 2018/0171103 A1 | 6/2018 | Kim et al. | | |
| 2019/0211183 A1 | 7/2019 | Kim et al. | | |
| 2019/0248982 A1 | 8/2019 | Kim et al. | | |
| 2021/0070965 A1 * | 3/2021 | Kim | ......................... | C08K 5/01 |
| 2021/0355069 A1 * | 11/2021 | Kim | ..................... | B01J 19/0013 |
| 2022/0177405 A1 * | 6/2022 | Makarczyk | .............. | C07C 67/54 |
| 2022/0185988 A1 * | 6/2022 | Kim | ..................... | C08K 5/0016 |
| 2023/0242737 A1 * | 8/2023 | Kim | ........................ | C08L 27/06 524/311 |

FOREIGN PATENT DOCUMENTS

| | | |
|---|---|---|
| CN | 1558927 A | 12/2004 |
| CN | 102408646 A | 4/2012 |
| CN | 104703961 A | 6/2015 |
| CN | 105037161 A | 11/2015 |
| CN | 107709429 A | 2/2018 |
| DE | 19927977 A1 | 12/2000 |
| JP | 2009-107996 A | 5/2009 |
| KR | 10-2001-0033257 A | 4/2001 |
| KR | 10-2003-0077970 A | 10/2003 |
| KR | 10-2017-0121060 A | 11/2017 |
| KR | 10-2018-0080689 A | 7/2018 |
| KR | 10-2018-0092888 A | 8/2018 |
| TW | 200304925 | 10/2003 |
| TW | 201833070 | 9/2018 |
| WO | 2010-027640 A1 | 3/2010 |
| WO | 2010-063740 A1 | 6/2010 |
| WO | 2014/053535 A2 | 4/2014 |
| WO | 2018-128314 A1 | 7/2018 |
| WO | 2018-147689 A1 | 8/2018 |

\* cited by examiner

*Primary Examiner* — Jane L Stanley

(74) *Attorney, Agent, or Firm* — Bryan Cave Leighton Paisner LLP

(57) ABSTRACT

A plasticizer composition which includes a lower non-hybrid-type cyclohexane triester, a lower hybrid-type cyclohexane triester, a higher hybrid-type cyclohexane triester, and a higher non-hybrid-type cyclohexane triester, wherein the alkyl groups of the cyclohexane triesters are a combination of C3-C6 alkyl groups and C7-C10 alkyl groups. When the plasticizer composition is applied to a resin, stress resistance and mechanical properties are maintained at an equivalent level or improved, migration properties, volatile loss characteristics, and plasticization efficiency are balanced, and light resistance and heat resistance are significantly improved.

11 Claims, No Drawings

CYCLOHEXANE TRIESTER BASED PLASTICIZER COMPOSITION AND RESIN COMPOSITION COMPRISING THE SAME

CROSS-REFERENCE TO RELATED APPLICATIONS

This application is a U.S. national stage of international Application No. PCT/KR2019/014322 filed Oct. 29, 2019, and claims priority to and the benefit of Korean Patent Application No. 10-2018-0129866, filed on Oct. 29, 2018, the disclosures of which are incorporated herein by reference in their entirety.

TECHNICAL FIELD

The present invention relates to: a cyclohexane triester-based plasticizer composition including various types of cyclohexane triesters; and a resin composition including the same.

BACKGROUND

Conventionally, in plasticizers, an alcohol and a polycarboxylic acid, such as phthalic acid or adipic acid, react to form a corresponding ester. In addition, in consideration of domestic and international regulations for phthalate-based plasticizers harmful to humans, there is ongoing research on plasticizer compositions that can replace phthalate-based plasticizers, such as terephthalate-based plasticizer compositions, adipate-based plasticizer compositions, and other polymer-based plasticizer compositions.

Meanwhile, there is an increasing demand for such environmentally-friendly products in all of the plastisol industry dealing with flooring, wallpaper, soft sheets, hard sheets, and the like, the calendering industry and the extrusion/injection-molding compounding industry, and to improve the quality characteristics, processability, and productivity of each finished product in this regard, it is necessary to use appropriate plasticizers in consideration of discoloration, migration properties, mechanical properties, and the like.

Depending on the characteristics required for each industry in various application areas as described above, such as tensile strength, an elongation rate, light resistance, migration properties, gelling properties, an absorption rate, or the like, a polyvinyl chloride (PVC) resin is mixed with an auxiliary material such as a plasticizer, a filler, a stabilizer, a viscosity-reducing agent, a dispersant, an antifoaming agent, a foaming agent, and the like.

For example, di(2-ethylhexyl) terephthalate (DEHTP), which is relatively inexpensive and most widely used among plasticizer compositions applicable to PVC, has been used, but in this case, high hardness or high sol viscosity is exhibited, the absorption rate of the plasticizer is relatively low, and migration properties and migration properties upon stress are poor.

As a remedy for this issue, it may be conceivable to apply a product of transesterification between DEHTP and butanol as a composition including DEHTP used as the plasticizer, but in this case, although plasticization efficiency may be improved, volatile loss, thermal stability, and the like and mechanical properties are slightly degraded, and therefore, an improvement in several properties is required. However, there is currently no solution other than to apply a general method of overcoming the above-described problems by further using other secondary plasticizers.

However, the use of a secondary plasticizer has disadvantages in that it becomes difficult to predict changes in properties, the secondary plasticizer may act as a factor that increases the unit cost of the product, the improvement of properties is not noticeable except in certain cases, and the secondary plasticizer may cause unexpected problems such as reduced compatibility with resins.

In addition, when a trimellitate-based material such as tri(2-ethylhexyl) trimellitate or triisononyl trimellitate is applied to improve the poor migration properties and poor volatile loss characteristics of the DEHTP product, although the migration properties or volatile loss characteristics may be improved, plasticization efficiency is lowered, and given the necessity to use a considerable amount of the trimellitate-based material to impart proper plasticizing properties to the resin, the unit price of the product becomes relatively high, thus making the commercialization of the product impossible.

Therefore, it is necessary to develop a product in which the poor properties of the existing products or of environmentally-friendly products aimed at improving the environmental disadvantages of phthalate-based products are overcome.

SUMMARY

The present invention is directed to providing a plasticizer composition, and more particularly, a plasticizer composition that includes various types of cyclohexane triesters and thus, in comparison to existing plasticizers, allows mechanical properties and stress resistance to be maintained at an equivalent level or improved and, at the same time, allows light resistance and heat resistance to be significantly improved while properly balancing migration properties, volatile loss properties, and plasticization efficiency.

One aspect of the present invention provides a cyclohexane triester-based plasticizer composition that includes, as cyclohexane triesters: a lower non-hybrid-type compound including a compound of Chemical Formula 1; a lower hybrid-type compound including two or more compounds of Chemical Formula 2; a higher hybrid-type compound including two or more compounds of Chemical Formula 3; and a higher non-hybrid-type compound including a compound of Chemical Formula 4:

[Chemical Formula 1]

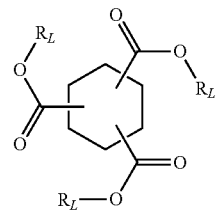

[Chemical Formula 2]

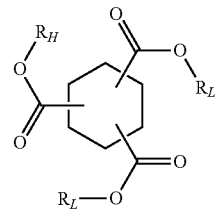

-continued

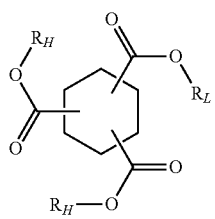
[Chemical Formula 3]

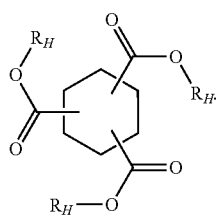
[Chemical Formula 4]

In Chemical Formulas 1 to 4, $R_L$ is a C3-C6 alkyl group, and $R_H$ is a C7-C10 alkyl group.

Another aspect of the present invention provides a resin composition which includes: a resin in an amount of 100 parts by weight; and the above-described plasticizer composition in an amount of 5 to 150 parts by weight.

The resin may be one or more selected from the group consisting of a straight vinyl chloride polymer, a paste vinyl chloride polymer, an ethylene vinyl acetate copolymer, an ethylene polymer, a propylene polymer, polyketone, polystyrene, polyurethane, natural rubber, synthetic rubber, and a thermoplastic elastomer.

When applied to a resin composition, the plasticizer composition according to one aspect of the present invention can allow mechanical properties and stress resistance to be maintained at an equivalent level or improved compared to existing plasticizers and, at the same time, can significantly improve light resistance and heat resistance while properly balancing migration properties, volatile loss characteristics and plasticization efficiency.

DETAILED DESCRIPTION

Terms and words used in this specification and claims should not be interpreted as being limited to commonly used meanings or meanings in dictionaries, and, based on the principle that the inventors can appropriately define concepts of terms to describe their invention in the best way, the terms and words should be interpreted with meanings and concepts which are consistent with the technological spirit of the present invention.

As used herein, the term "composition" encompasses not only a mixture of materials making up the relevant composition but also reaction products and decomposition products formed from the materials of the relevant composition.

As used herein, the prefix "iso-" is used to represent an alkyl group having a C1 methyl group or C2 ethyl group attached as a branched chain to the main chain thereof, and is generally used to represent an alkyl group having a methyl branch attached to a terminus. However, unless otherwise specified, the prefix "iso-" may be used herein to generically represent alkyl groups having a methyl group or ethyl group attached as a branched chain to the main chain thereof, including those having a methyl group or ethyl group attached to a terminus.

As used herein, the term "isononyl group" may refer to an alkyl group that has a total of nine carbon atoms since one or more among one or two methyl groups, one ethyl group and one propyl group are substituted in the main chain thereof, forming a branch, and may be a term used to collectively refer to, for example, a 2-methyloctyl group, a 3-methyloctyl group, a 4-methyloctyl group, a 5-methyloctyl group, a 6-methyloctyl group, a 3-ethylheptyl group, a 2-ethylheptyl group, a 2,5-dimethylheptyl group, a 2,3-dimethylheptyl group, a 4,5-dimethylheptyl group, a 3-ethyl-4-methylhexyl group, a 2-ethyl-4-methylhexyl group, a 2-propylhexyl group, and the like. Commercially used isononanols (CAS Nos. 68526-84-1 and 27458-94-2) may refer to compositions of isomers having a degree of branching of 1.2 to 1.9, and some of these commercial alcohols may also include an n-nonyl group.

As used herein, the term "straight vinyl chloride polymer" may refer to a type of vinyl chloride polymer that has been polymerized through suspension polymerization, bulk polymerization, or the like, and may refer to a polymer which has the form of porous particles of several tens to hundreds of micrometers in size and in which a large number of pores are distributed and which has no cohesiveness and exhibits excellent flowability.

As used herein, the term "paste vinyl chloride polymer" may refer to a type of vinyl chloride polymer that has been polymerized through microsuspension polymerization, micro-seeded polymerization, emulsion polymerization, or the like, and may refer to a polymer which has the form of fine, dense, and pore-free particles of several tens to several thousands of nanometers in size and which has cohesiveness and exhibits poor flowability.

The terms "comprising," "including," "containing," "having," and derivatives thereof are not intended to exclude the presence of any additional components, steps, or procedures, whether they are specifically disclosed or not. To avoid any uncertainty, all compositions claimed through the use of the terms "comprising," "including," "containing," and "having," whether polymers or otherwise, may include any additional additives, adjuvants, or compounds unless otherwise stated. In contrast, the term "consisting essentially of" excludes any other component, step, or procedure from the scope of any subsequent description, and excludes those that are not essential to operability. The terms "consisting of" excludes any element, step, or procedure that is not specifically described or listed.

In the present specification, the amount of components in a composition are analyzed by carrying out measurements through gas chromatography using a gas chromatography instrument manufactured by Agilent Technologies Inc. (Agilent 7890 GC; column: HP-5, carrier gas: helium (flow rate: 2.4 mL/min), detector: F.I.D, injection volume: 1 µL, initial value: 70° C./4.2 min, end value: 280° C./7.8 min, programmed rate: 15° C./min).

In the present specification, "hardness" refers to Shore hardness (Shore "A" and/or Shore "D") as measured at 25° C. in accordance with ASTM D2240. The hardness is measured for 10 seconds using a 3T test specimen, and may be an index for evaluating plasticization efficiency, and smaller hardness values indicate better plasticization efficiency.

In the present specification, "tensile strength" is measured in accordance with ASTM D638 by pulling a 1T test specimen at a cross head speed of 200 mm/min using a universal testing machine (UTM) (4466 manufactured by Instron) and determining a time point at which the test specimen is broken, and is calculated by the following Equation 1.

Tensile strength (kgf/cm²)=Load (kgf)/Thickness (cm)×Width (cm) [Equation 1]

In the present specification, "elongation rate" is measured in accordance with ASTM D638 by pulling a 1T test specimen at a cross head speed of 200 mm/min using the UTM and determining a time point at which the test specimen is broken, and is calculated by the following Equation 2:

Elongation rate(%)=Length after elongation/Initial length×100. [Equation 2]

In the present specification, "migration loss" is measured in accordance with KSM-3156 as follows. A test specimen having a thickness of 2 mm or more is prepared, glass plates are attached to both sides of the test specimen, and a load of 1 kgf/cm² is applied thereto. Subsequently, the test specimen is maintained in a hot-air convection oven (80° C.) for 72 hours and then taken out of the oven and cooled at room temperature for 4 hours. After removing the glass plates attached to both sides of the test specimen, the weights of the specimen plate before and after being maintained in the oven along with the glass plates are measured, and migration loss is calculated by the following Equation 3:

Migration loss(%)={(Initial weight of test specimen at room temperature−Weight of test specimen after being maintained in oven)/Initial weight of test specimen at room temperature}×100. [Equation 3]

In the present specification, "volatile loss" is determined by processing a test specimen at 121° C. for 72 hours, weighing the test specimen, and calculated by the following Equation 4:

Volatile loss (wt %)={(Initial weight of test specimen−Weight of test specimen after being processed)/Initial weight of test specimen}×100. [Equation 4]

The details of the above-described various measurement conditions, such as temperature, rotation speed, time, and the like, may vary from case to case, and when there is a difference in details from those described above, clear descriptions of the measurement methods and conditions will be provided separately.

Hereinafter, the present invention will be described in more detail to facilitate understanding of the present invention.

According to one exemplary embodiment of the present invention, the plasticizer composition includes, as cyclohexane triesters: a lower non-hybrid-type cyclohexane triester including a compound of Chemical Formula 1; a lower hybrid-type cyclohexane triester including two or more compounds of Chemical Formula 2; a higher hybrid-type cyclohexane triester including two or more compounds of Chemical Formula 3; and a higher non-hybrid-type cyclohexane triester including a compound of Chemical Formula 4:

[Chemical Formula 1]
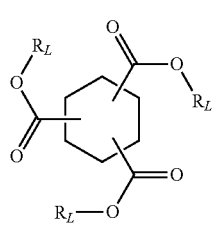

[Chemical Formula 2]
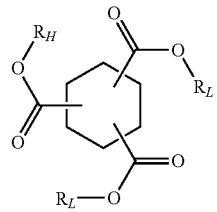

[Chemical Formula 3]
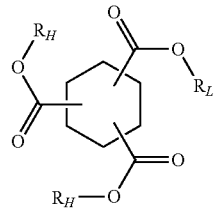

[Chemical Formula 4]
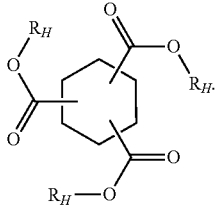

In Chemical Formulas 1 to 4, $R_L$ is a C3-C6 alkyl group, and $R_H$ is a C7-C10 alkyl group.

According to one exemplary embodiment of the present invention, the plasticizer composition includes a total of four types of cyclohexane triesters, wherein the four types of cyclohexane triesters include: a lower non-hybrid-type cyclohexane triester which includes alkyl groups having a smaller carbon number attached thereto; a lower hybrid-type cyclohexane triester which includes alkyl groups having a smaller carbon number attached to two ester groups and an alkyl group having a larger carbon number attached to a remaining ester group; a higher hybrid-type cyclohexane triester which includes, unlike the lower hybrid-type cyclohexane triester, alkyl groups having a larger carbon number attached to two ester groups; and a higher non-hybrid-type cyclohexane triester which includes alkyl groups having a larger carbon number attached thereto.

Here, the cyclohexane triester may refer to a compound which includes ester groups attached to carbons 1, 2, and 4 of cyclohexane, and the term "alkyl groups attached to . . . " or "attached alkyl groups" may refer to alkyl groups that are attached to the ester groups attached to the cyclohexane.

In addition, the terms "non-hybrid" and "hybrid" are used to distinguish whether the alkyl groups attached to the three ester groups have the same carbon number or different carbon numbers. When all of the alkyl groups attached to the three ester groups have the same carbon number, the cyclohexane triester may be referred to as being "non-hybrid," and when at least one of the alkyl groups attached to the three ester groups has a different carbon number from the rest, the cyclohexane triester may be referred to as being "hybrid."

In addition, the terms "higher" and "lower" may be used to indicate the relative magnitude of the carbon number of an alkyl group, and are named considering how a cyclohexane triester differs from other types of cyclohexane triesters in terms of the magnitude of carbon numbers of main alkyl groups attached to three ester groups thereof, and are not intended to absolutely refer to a specific alkyl group.

According to one exemplary embodiment of the present invention, the plasticizer composition may include the above-described four types of cyclohexane triesters, and the compound of Chemical Formula 1 that belongs to lower non-hybrid-type cyclohexane triesters may be represented by Chemical Formula 1a, and the compound of Chemical Formula 4 that belongs to higher non-hybrid-type cyclohexane triesters may be represented by Chemical Formula 4a:

[Chemical Formula 1a]

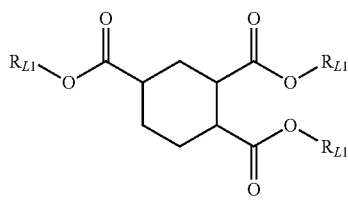

[Chemical Formula 4a]

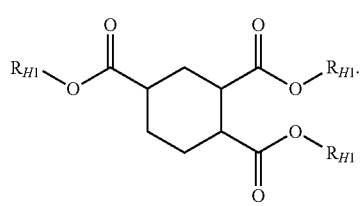

In Chemical Formulas 1a and 4a, $R_{L1}$ is a C3-C6 alkyl group, and $R_{H1}$ is a C7-C10 alkyl group.

The lower non-hybrid-type cyclohexane triester may be a cyclohexane triester including three ester groups to which the same C3-C6 alkyl groups (i.e., alkyl groups having a smaller carbon number) are attached, and the higher non-hybrid-type cyclohexane triester may be a cyclohexane triester including three ester groups to which the same C7-C10 alkyl groups are attached. In these cyclohexane triesters, the ester groups may be attached to carbons 1, 2, and 4 of cyclohexane.

Meanwhile, cyclohexane triesters of a hybrid type, and not a non-hybrid type, may be classified into three types, namely ortho, meta, and para types, according to the positional relationship of the attached alkyl groups.

For example, the lower hybrid-type cyclohexane triesters may include a lower hybrid ortho-type cyclohexane triester, a lower hybrid meta-type cyclohexane triester, and a lower hybrid para-type cyclohexane triester which may be represented by Chemical Formulas 2a, 2b, and 2c, respectively, wherein the ortho, meta, and para types are named based on alkyl groups of the same kind:

[Chemical Formula 2a]

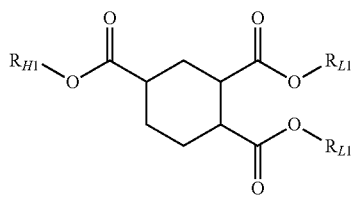

[Chemical Formula 2b]

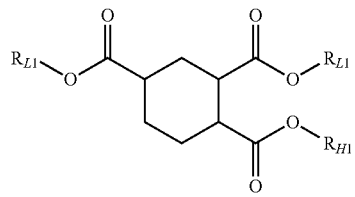

[Chemical Formula 2c]

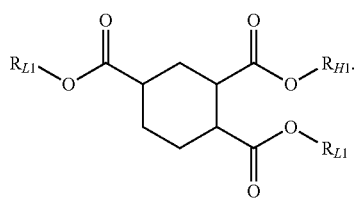

In Chemical Formulas 2a to 2c, $R_{L1}$ is a C3-C6 alkyl group, and $R_{H1}$ is a C7-C10 alkyl group.

In addition, the higher hybrid-type cyclohexane triesters may include a higher hybrid ortho-type cyclohexane triester, a higher hybrid meta-type cyclohexane triester, and a higher hybrid para-type cyclohexane triester which may be represented by Chemical Formulas 3a, 3b, and 3c, respectively, wherein the ortho, meta, and para types are named based on alkyl groups of the same kind:

[Chemical Formula 3a]

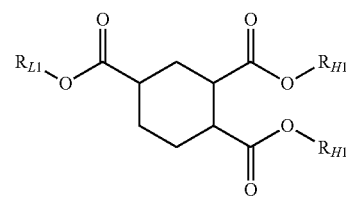

[Chemical Formula 3b]

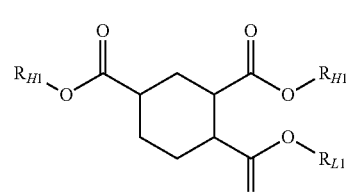

[Chemical Formula 3c]

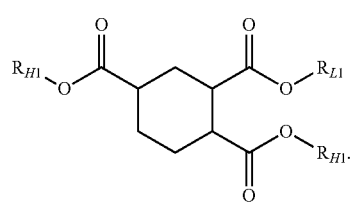

In Chemical Formulas 3a to 3c, $R_{L1}$ is a C3-C6 alkyl group, and $R_{H1}$ is a C7-C10 alkyl group.

Since there are four types of cyclohexane triesters included therein as described above, the plasticizer composition according to one exemplary embodiment of the present invention can realize an excellent effect through a combination of attached alkyl groups that is suitable for each cyclohexane triester type. Specifically, due to the balance between the alkyl groups of a lower non-hybrid-type cyclohexane triester and the alkyl groups of a higher non-hybrid-type cyclohexane triester and the presence of different hybrid-type cyclohexane triesters in the composition, plasticization efficiency and properties such as migration properties/volatile loss characteristics can be balanced, mechanical properties such as tensile strength and an elongation rate can be improved, stress resistance can be maintained at an equivalent level or improved, and, due to the interaction of the four types of cyclohexane triesters included in the composition, a significant improvement in light resistance can be achieved.

Accordingly, it may be possible to realize products in which volatile loss characteristics have been further improved while the environmental issues of existing phthalate-based products have been eliminated, and it may be possible to realize products in which the migration properties and volatile loss characteristics of existing terephthalate-based products have been significantly improved and light resistance and heat resistance have been greatly improved compared to those of existing commercialized products.

To realize the above-described effects more optimally and preferably, it may be important to satisfy the $R_L$ and $R_H$ conditions defined in Chemical Formulas 1 to 4, Chemical Formulas 1a and 4a, and the like. Since $R_L$ may be the same as $R_{L1}$, and $R_H$ may be the same as $R_{H1}$, $R_L$ and $R_H$ will be representatively described hereinafter, and the descriptions may be equally applied to the definitions of $R_{L1}$ and $R_{H1}$.

As defined above, $R_L$ and $R_H$ may be a C3-C6 alkyl group and a C7-C10 alkyl group, respectively. Since these carbon numbers are factors that can determine the interaction between different types of cyclohexane triesters included in the cyclohexane triester-based plasticizer composition and the weight of the entire composition, it may be necessary to satisfy the above-described conditions to achieve the above-described effects. Here, the alkyl group may be linear or branched.

$R_L$ is preferably a C4-C6 alkyl group, more preferably a C5 or C6 alkyl group. In addition, $R_H$ is preferably a C7-C10 alkyl group, more preferably a C8-C10 alkyl group, even more preferably a C8 or C9 alkyl group. When the above-described ranges are satisfied, the effect of realizing stress resistance and light resistance can be further maximized, and an effect of improving tensile strength and an elongation rate compared to a trimellitate having the same alkyl groups can be provided.

In addition, the combination of $R_L$ and $R_H$ may be an important factor just as whether the $R_L$ and the $R_H$ satisfy the above-described carbon number ranges is important, and, if possible, it is preferred that the $R_L$ and the $R_H$ are selected such that the sum thereof is no more than 15 and no less than 12. For example, when a C6 alkyl group is selected as $R_L$, it is preferred that an alkyl group having at most nine carbon atoms is selected as $R_H$, and when a C4 alkyl group is selected as $R_L$, it is preferred that an alkyl group having at least eight carbon atoms is selected as $R_H$. However, although the combination of carbon numbers of these alkyl groups matters in terms of realizing a desirable effect, even if the sum of carbon numbers does not meet the above-described condition, it may not be impossible to achieve the desired effect of the present invention.

More specifically, in Chemical Formulas 1 to 4, $R_L$ may be selected from the group consisting of a propyl group, a butyl group, an isobutyl group, an n-pentyl group, an isopentyl group, an n-hexyl group, and an isohexyl group, and $R_H$ may be selected from the group consisting of an n-heptyl group, an isoheptyl group, an n-octyl group, an isooctyl group, a 2-ethylhexyl group, an n-nonyl group, an isononyl group, an n-decyl group, an isodecyl group, and a 2-propylheptyl group. Here, each of the isobutyl group, the isopentyl group, the isohexyl group, the isoheptyl group, the isooctyl group, the isononyl group, and the isodecyl group may refer to an alkyl group having a methyl group or ethyl group as a branched chain, and the number of methyl groups attached as a branched chain may be one or two.

More preferably, in Chemical Formulas 1 to 4, $R_L$ is selected from the group consisting of a butyl group, an isobutyl group, an n-pentyl group, an isopentyl group, an n-hexyl group, and an isohexyl group, and $R_H$ is selected from the group consisting of an n-heptyl group, an isoheptyl group, a 2-ethylhexyl group, an isononyl group, an isodecyl group, and a 2-propylheptyl group, and when alkyl groups satisfying the above-described preferred carbon number conditions are selected, the effect of the present invention can be improved in a more preferred way.

The above-described alkyl groups specified by specific names, which are alkyl groups that may be selected as $R_L$ and $R_H$, have been selected with overall consideration given to whether the alkyl groups are branched or linear and, if branched, how many carbon atoms are present and the like. Although the extent to which the effect of the present invention is improved by the above-described carbon number range and the extent to which the effect of the present invention is improved by applying the specifically specified alkyl groups may be independent of each other, the tendencies that the effects are improved are the same in that the effects as described above are achieved.

According to one exemplary embodiment of the present invention, the plasticizer composition includes four types of cyclohexane triesters as described above, wherein each of the four types of cyclohexane triesters may be the lower non-hybrid-type cyclohexane triester which is included in an amount of 0.01 to 70 wt %, the lower hybrid-type cyclohexane triester which is included in an amount of 5 to 70 wt %, the higher hybrid-type cyclohexane triester which is included in an amount of 5 to 70 wt %, and the higher non-hybrid-type cyclohexane triester which is included in an amount of 0.01 to 70 wt %. Alternatively, the four types of cyclohexane triesters may be the lower non-hybrid-type cyclohexane triester which is included in an amount of 0.1 to 60 wt %, the lower hybrid-type cyclohexane triester which is included in an amount of 10 to 60 wt %, the higher hybrid-type cyclohexane triester which is included in an amount of 10 to 60 wt %, and the higher non-hybrid-type cyclohexane triester which is included in an amount of 0.1 to 60 wt %. Each of the four types of cyclohexane triesters is preferably included in an amount of 0.5 to 50 wt %, 10 to 50 wt %, 10 to 50 wt %, and 0.5 to 50 wt %, more preferably included in an amount of 0.5 to 40 wt %, 10 to 50 wt %, 10 to 50 wt %, and 0.5 to 40 wt %, even more preferably included in an amount of 0.5 to 35 wt %, 10 to 40 wt %, 15 to 50 wt %, and 1 to 40 wt %.

When components of the plasticizer composition of the present invention are provided in the above-described ranges, not only can the productivity in a manufacturing process be increased considering the equivalence ratio of materials used as reactants, the actual yield or conversion rate of the reaction, or the like, but also the degradation of mechanical properties such as the above-described tensile strength and elongation rate can be prevented, and the advantage that quality can be freely adjusted by optimizing properties such as plasticization efficiency, volatile loss, migration properties, absorption rate, and the like can be exercised.

According to one exemplary embodiment of the present invention, the method for preparing the plasticizer composition is not particularly limited, and any method known in the art and capable of preparing the above-described plasticizer composition may be used.

That is, the plasticizer composition of the present invention can be prepared through a suitable combination of hydrogenation, direct esterification, and transesterification, for example, by hydrogenating a trimellitate composition which has been prepared through the direct esterification of trimellitic acid carried out using two or more types of alcohols, or by hydrogenating a trimellitate composition which has been prepared through transesterification between a trimellitate and one type of alcohol.

In addition, the order of esterification and hydrogenation may be reversed, such that the plasticizer composition of the present invention may be prepared by a method of hydrogenating trimellitic acid prior to esterification and then carrying out direct esterification using the resulting cyclohexane tricarboxylic acid and two or more types of alcohols as reactants, or by a method of hydrogenating a trimellitate prior to esterification and then carrying out transesterification using the resulting cyclohexane triester and one type of alcohol as reactants.

According to one exemplary embodiment of the present invention, the plasticizer composition is a material prepared through a suitable combination of the above-described esterification and hydrogenation, and the preparation method thereof is not particularly limited as long as the above-described conditions are met.

For example, the direct esterification may include: adding trimellitic acid or cyclohexane tricarboxylic acid and two or more types of alcohols, followed by adding a catalyst and then reacting under a nitrogen atmosphere; removing an unreacted alcohol and neutralizing an unreacted acid; and carrying out dehydration through vacuum distillation and filtration.

The alcohol may be a primary alcohol having alkyl groups whose carbon numbers comply with the carbon numbers of $R_H$ and $R_L$ of Chemical Formulas 1 to 4, in which case the primary alcohol having the alkyl group $R_L$ may serve as a major factor in determining the ratio between components in the prepared composition. The usage amount of the alcohol may range from 150 to 500 mol %, 200 to 400 mol %, 200 to 350 mol %, 250 to 400 mol %, or 270 to 330 mol % based on 100 mol % of terephthalic acid, and by way of controlling the proportion of this alcohol, the ratio between components in the final composition can be controlled.

The catalyst may be, for example, one or more selected from among acidic catalysts such as sulfuric acid, hydrochloric acid, phosphoric acid, nitric acid, para-toluenesulfonic acid, methanesulfonic acid, ethanesulfonic acid, propanesulfonic acid, butanesulfonic acid, an alkyl sulfate, and the like, metal salts such as aluminum lactate, lithium fluoride, potassium chloride, cesium chloride, calcium chloride, iron chloride, aluminum phosphate, and the like, metal oxides such as a heteropoly acid and the like, natural/synthetic zeolites, cation and anion exchange resins, and organic metals such as a tetra alkyl titanate and polymers thereof. As a specific example, the catalyst may be a tetra alkyl titanate. Preferably, an acid catalyst having a low activation temperature, such as para-toluenesulfonic acid, methanesulfonic acid, or the like, is appropriate as the catalyst.

The usage amount may vary according to the type of catalyst. For example, the usage amount may range from 0.01 to 5 wt %, 0.01 to 3 wt %, 1 to 5 wt %, or 2 to 4 wt % based on 100 wt % of total reactants in the case of a homogeneous catalyst, or may range from 5 to 200 wt %, 5 to 100 wt %, 20 to 200 wt %, or 20 to 150 wt % of the total amount of reactants in the case of a heterogeneous catalyst.

In one example, the reaction temperature may range from 180 to 280° C., 200 to 250° C., or 210 to 230° C.

In another example, the transesterification may be a reaction between, for example, tri(2-ethylhexyl) trimellitate (which may be a cyclohexane triester if hydrogenation is carried out first, although a trimellitate will be taken as an example hereinafter for the purpose of illustration) and an alcohol such as butanol or the like. Here, the alkyl groups of the trimellitate and the alcohol may be interchanged with each other, but, if possible, it is preferred that the alkyl group corresponding to $R_H$ has been derived from the trimellitate and the alkyl group corresponding to $R_L$ has been derived from the alcohol.

As used herein, the "transesterification" refers to a reaction in which an alcohol reacts with an ester as shown in Reaction Scheme 1, causing the R" of the ester to be exchanged with the R' of the alcohol as shown in Reaction Scheme 1:

[Reaction Scheme 1]

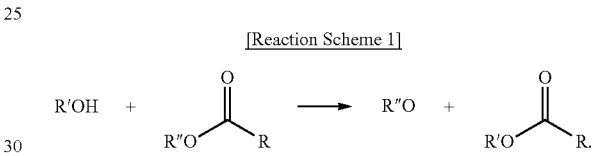

According to one exemplary embodiment of the present invention, when the transesterification is carried out, four types of ester compositions may result due to four possible outcomes, such as: the alkoxide of the alcohol attacks three of the carbons present in ester (RCOOR") groups of the ester compound; the alkoxide of the alcohol attacks two of the carbons present in ester (RCOOR") groups of the ester compound; the alkoxide of the alcohol attacks one of the carbons present in ester (RCOOR") groups of the ester compound; and no reaction has occurred.

However, in the case of the cyclohexane triesters included in the plasticizer composition of the present invention, depending on the bonding position of the ester groups, two of the ester groups may be involved in the exchange, or one of the ester groups may be involved in the exchange. Since three types of compounds can be formed for each of the above-described cases, there may be up to eight types of compounds present in the final composition.

In addition, the transesterification has the advantage that a waste-water issue is not caused unlike in the case of acid-alcohol esterification, and since the transesterification can be carried out in the absence of a catalyst, the problem in using an acid catalyst can be avoided.

The composition ratio of the mixture prepared by the transesterification may be controlled by the addition amount of the alcohol. The addition amount of the alcohol may be 0.1 to 89.9 parts by weight, specifically 3 to 50 parts by weight, more specifically 5 to 40 parts by weight, relative to 100 parts by weight of the trimellitate compound. For reference, what determines the ratio between components in the final composition may be the addition amount of the alcohol just as in the above-described direct esterification.

That is, as more alcohol is added, since a larger mole fraction of the trimellitate compound will participate in the transesterification, the amount of trimellitate which is a product will increase in the mixture, and the amount of unreacted trimellitate will decrease accordingly.

According to one exemplary embodiment of the present invention, the molar ratio of reactants trimellitate and alcohol may be, for example, 1:0.005 to 5.0, 1:0.05 to 2.5, or 1:0.1 to 1.0. Within this range, processability and economic feasibility can be excellent, and a plasticizer composition capable of realizing the above-described effect can be obtained.

According to one exemplary embodiment of the present invention, the transesterification is carried out at a reaction temperature of 120° C. to 190° C., preferably 135° C. to 180° C., more preferably 141° C. to 179° C., for 10 minutes to 10 hours, preferably 30 minutes to 8 hours, more preferably 1 to 6 hours. Within these temperature and time ranges, the ratio between components of the final plasticizer composition can be efficiently controlled. In this case, the reaction time may be counted from the time point at which the temperature of reactants being heated reaches the reaction temperature.

The transesterification may be carried out in the presence of an acid catalyst or a metal catalyst, and in this case, the reaction time can be shortened.

The acid catalyst may be, for example, sulfuric acid, methanesulfonic acid, p-toluenesulfonic acid, or the like, and the metal catalyst may be, for example, an organometallic catalyst, a metal oxide catalyst, a metal salt catalyst, or a metal itself.

The metal component may be, for example, any one or a mixture of two or more selected from the group consisting of tin, titanium, and zirconium.

In addition, the method may further include, after the transesterification, removing unreacted alcohol, reaction by-products, and the like through distillation. The distillation may be, for example, two-stage distillation in which the alcohol and the reaction by-products are separated in separate stages using a difference in boiling points. In another example, the distillation may be mixed distillation. In this case, an ester-based plasticizer composition can be obtained, with a desired composition ratio thereof being relatively stably ensured. Here, the mixed distillation refers to the simultaneous distillation of unreacted alcohol and reaction by-products.

Hydrogenation is a reaction in which the aromaticity of the benzene ring of a trimellitate is removed as hydrogen is added, which occurs in the presence of a metal catalyst, and which may be a kind of a reduction reaction.

In the above-described hydrogenation, the trimellitate is reacted with the hydrogen in the presence of the metal catalyst to synthesize a cyclohexane triester or cyclohexane tricarboxylic acid, and the reaction conditions thereof may be any conventional reaction conditions capable of hydrogenating only the benzene ring without affecting the carbonyl group (an ester or carboxylic acid) substituted in the benzene.

The hydrogenation may be carried out using an additional organic solvent such as ethanol or the like, but the present invention is not limited thereto. As the metal catalyst, a Rh/C catalyst, a Pt catalyst, a Pd catalyst, and the like which are generally used to hydrogenate a benzene ring may be used, but there is no limitation, and any metal catalyst capable of allowing the above-described hydrogenation may be used.

Although esterification and hydrogenation have been described so far as methods of preparing the plasticizer composition according to one exemplary embodiment of the present invention, since hydrogenation has the disadvantage that the use of relatively expensive catalyst metals and severe reaction conditions may lead to an increase in unit cost, if possible, it may be more preferable to prepare the plasticizer composition through esterification using a hydrogenated raw material.

According to another aspect of the present invention, there is provided a resin composition including the above-described plasticizer composition and a resin.

As the resin, resins known in the art may be used. For example, one or a mixture of two or more selected from the group consisting of a straight vinyl chloride polymer, a paste vinyl chloride polymer, an ethylene vinyl acetate copolymer, an ethylene polymer, a propylene polymer, polyketone, polystyrene, polyurethane, natural rubber, synthetic rubber, and a thermoplastic elastomer may be used, but the present invention is not limited thereto.

The plasticizer composition may be included in an amount of 5 to 150 parts by weight, preferably 5 to 130 parts by weight, or 10 to 120 parts by weight, relative to 100 parts by weight of the resin.

Generally, the resin composition to which the plasticizer composition is applied may be formed into a resin product through melt processing or plastisol processing, and a resin for melt processing and a resin for plastisol processing may be prepared differently by different polymerization methods.

For example, a vinyl chloride polymer to be used in melt processing is prepared by suspension polymerization or the like and thus is used as a solid resin particle having a large particle diameter, and such a vinyl chloride polymer is referred to as a straight vinyl chloride polymer, and a vinyl chloride polymer to be used in plastisol processing is prepared by emulsion polymerization or the like and thus is used as a fine resin particle in a sol state, and such a vinyl chloride polymer is referred to as a paste vinyl chloride resin.

In the case of the straight vinyl chloride polymer, the plasticizer is preferably included in an amount ranging from 5 to 80 parts by weight relative to 100 parts by weight of the polymer, and in the case of the paste vinyl chloride polymer, the plasticizer is preferably included in an amount ranging from 40 to 120 parts by weight relative to 100 parts by weight of the polymer.

The resin composition may further include a filler. The filler may be used in an amount of 0 to 300 parts by weight, preferably 50 to 200 parts by weight, more preferably 100 to 200 parts by weight, relative to 100 parts by weight of the resin.

As the filler, fillers known in the art may be used without particular limitation. For example, the filler may be one or a mixture of two or more selected from the group consisting of silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate, and barium sulfate.

In addition, the resin composition may further include other additives such as a stabilizer and the like as necessary. Each of the additives such as a stabilizer and the like may be included, for example, in an amount of 0 to 20 parts by weight, preferably 1 to 15 parts by weight, relative to 100 parts by weight of the resin. As the stabilizer, for example, a calcium-zinc (Ca—Zn)-based stabilizer such as a complex stearate of calcium and zinc or the like may be used, but the present invention is not particularly limited thereto.

The resin composition may be applied to both melt processing and plastisol processing as described above, wherein the melt processing may be, for example, calendering, extrusion, or injection-molding, and the plastisol processing may be coating processing or the like.

EXAMPLES

Hereinafter, the present invention will be described in more detail by way of examples. However, the examples of the present invention may have various modifications, and the scope of the present invention should not be construed as being limited to the examples described below. The examples of the present invention are provided to more completely explain the present invention to those of ordinary skill in the art.

Example 1

After adding 500 g of cyclohexane 1,2,4-tricarboxylic anhydride, 1,280 g of 2-ethylhexanol and 2 g of tetrabutyl titanate (TnBT) to a reactor equipped with a stirrer, a condenser and a decanter, esterification was initiated under a nitrogen atmosphere. After terminating the esterification, the unreacted alcohol was removed, and then transesterification was carried out by adding 384 g of n-butanol. After terminating the transesterification, the catalyst and the product were neutralized with an aqueous alkali solution, and the unreacted alcohol and water were purified, and thereby a composition including tri(n-butyl) cyclohexane 1,2,4-triester, di(n-butyl)(2-ethylhexyl) cyclohexane 1,2,4-triester, di(2-ethylhexyl)(n-butyl) cyclohexane 1,2,4-triester, and tri(2-ethylhexyl) cyclohexane 1,2,4-triester in an amount of 1.0 wt %, 15.0 wt %, 45.6 wt %, and 38.4 wt %, respectively, was finally obtained.

Example 2

Esterification was carried out in the same manner as in Example 1 except that 1,440 g of isononanol was added instead of the 2-ethylhexanol used in Example 1, and thereby a composition including tri(n-butyl) cyclohexane 1,2,4-triester, di(n-butyl)isononyl cyclohexane 1,2,4-triester, diisononyl(n-butyl) cyclohexane 1,2,4-triester, and triisononyl cyclohexane 1,2,4-triester in an amount of 1.5 wt %, 16.0 wt %, 47.0 wt %, and 35.5 wt %, respectively, was obtained.

Example 3

Esterification was carried out in the same manner as in Example 1 except that 420 g of n-pentanol was added instead of the n-butanol used in Example 1, and thereby a composition including tri(n-pentyl) cyclohexane 1,2,4-triester, di(n-pentyl)(2-ethylhexyl) cyclohexane 1,2,4-triester, di(2-ethylhexyl)(n-pentyl) cyclohexane 1,2,4-triester, and tri(2-ethylhexyl) cyclohexane 1,2,4-triester in an amount of 3.7 wt %, 25.0 wt %, 45.2 wt %, and 26.1 wt %, respectively, was obtained.

Example 4

Esterification was carried out in the same manner as in Example 2 except that 570 g of n-pentanol was added instead of the n-butanol used in Example 2, and thereby a composition including tri(n-pentyl) cyclohexane 1,2,4-triester, di(n-pentyl)isononyl cyclohexane 1,2,4-triester, diisononyl(n-pentyl) cyclohexane 1,2,4-triester, and triisononyl cyclohexane 1,2,4-triester in an amount of 4.9 wt %, 35.7 wt %, 40.5 wt %, and 18.9 wt %, respectively, was obtained.

Example 5

Esterification was carried out in the same manner as in Example 1 except that, unlike in Example 1, 500 g of cyclohexane 1,2,4-tricarboxylic anhydride, 780 g of 2-ethylhexanol, 410 g of n-hexanol, and 2 g of TnBT were added. After terminating the esterification, the neutralization of the catalyst and the product and purification were carried out, and thereby a composition including tri(n-hexyl) cyclohexane 1,2,4-triester, di(n-hexyl)(2-ethylhexyl) cyclohexane 1,2,4-triester, di(2-ethylhexyl)(n-hexyl) cyclohexane 1,2,4-triester, and tri(2-ethylhexyl) cyclohexane 1,2,4-triester in an amount of 6.3 wt %, 36.1 wt %, 42.7 wt %, and 14.9 wt %, respectively, was obtained.

Example 6

Esterification was carried out in the same manner as in Example 1 except that, unlike in Example 1, 500 g of cyclohexane 1,2,4-tricarboxylic anhydride, 576 g of isononanol, 612 g of hexanol, and 2 g of TnBT were added. After terminating the esterification, the neutralization of the catalyst and the product and purification were carried out, and thereby a composition including trihexyl cyclohexane 1,2,4-triester, dihexylisononyl cyclohexane 1,2,4-triester, di(isononyl)hexyl cyclohexane 1,2,4-triester, and triisononyl cyclohexane 1,2,4-triester in an amount of 12.5 wt %, 47.0 wt %, 38.1 wt %, and 2.4 wt %, respectively, was obtained.

Example 7

Esterification was carried out in the same manner as in Example 1 except that 1,600 g of 2-propylheptanol was added instead of the 2-ethylhexanol used in Example 1 and that 550 g of butanol was added, and thereby a composition including tri(n-butyl) cyclohexane 1,2,4-triester, di(n-butyl)(2-propylheptyl) cyclohexane 1,2,4-triester, di(2-propylheptyl)(n-butyl) cyclohexane 1,2,4-triester, and tri(2-propylheptyl) cyclohexane 1,2,4-triester in an amount of 5.2 wt %, 37.6 wt %, 38.7 wt %, and 18.5 wt %, respectively, was obtained.

Example 8

Reactions were carried out in such an order that esterification was first carried out using n-pentanol instead of the n-butanol used in Example 1 and transesterification was subsequently carried out using isononanol. After terminating the esterification by adding 500 g of cyclohexane 1,2,4-tricarboxylic anhydride, 900 g of n-pentanol, and 2 g of TnBT, the unreacted alcohol was removed, and then transesterification was carried out by adding 280 g of isononanol, and thereby a composition including tri(n-pentyl) cyclohexane 1,2,4-triester, di(n-pentyl)isononyl cyclohexane 1,2,4-triester, diisononyl(n-pentyl) cyclohexane 1,2,4-triester, and triisononyl cyclohexane 1,2,4-triester in an amount of 31.6 wt %, 41.0 wt %, 24.3 wt %, and 3.1 wt %, respectively, was finally obtained.

Example 9

The reactions were carried out in the same manner as in Example 8 except that 1,020 g of n-hexanol was added instead of n-pentanol and that 250 g of 2-ethylhexanol was added instead of isononanol, and thereby a composition including tri(n-hexyl) cyclohexane 1,2,4-triester, di(n-hexyl)(2-ethylhexyl) cyclohexane 1,2,4-triester, di(2-ethylhexyl)(n-hexyl) cyclohexane 1,2,4-triester, and tri(2-ethylhexyl) cyclohexane 1,2,4-triester in an amount of 33.6 wt %, 40.8 wt %, 20.5 wt %, and 5.1 wt %, respectively, was finally obtained.

Comparative Example 1

Diisononyl phthalate (DINP) manufactured by LG Chem Ltd. was used as a plasticizer composition.

Comparative Example 2

LGFLEX GL300™ manufactured by LG Chem Ltd., which is di(2-ethylhexyl) terephthalate (DEHTP), was used as a plasticizer composition.

Comparative Example 3

TOTM manufactured by LG Chem Ltd., which is tri(2-ethylhexyl) trimellitate (TEHTM), was used as a plasticizer composition.

Comparative Example 4

Triisononyl trimellitate (TINTM) manufactured by LG Chem Ltd. was used as a plasticizer composition.

Comparative Example 5

By using trimellitic anhydride instead of the cyclohexane 1,2,4-tricarboxylic anhydride used in Example 1 and using 2-ethylhexanol and n-butanol as raw materials, a composition including tri(n-butyl) trimellitate, di(n-butyl)(2-ethylhexyl) trimellitate, di(2-ethylhexyl)(n-butyl) trimellitate, and tri(2-ethylhexyl) trimellitate in an amount of 2.2 wt %, 11.4 wt %, 42.6 wt %, and 43.8 wt %, respectively, was finally obtained.

Comparative Example 6

The reactions were carried out in the same manner as in Comparative Example except that n-hexanol was used instead of 2-ethylhexanol, and thereby a composition including tri(n-butyl) trimellitate, di(n-butyl)(n-hexyl) trimellitate, di(n-hexyl)(n-butyl) trimellitate, and tri(n-hexyl) trimellitate in an amount of 3.8 wt %, 14.3 wt %, 44.2 wt %, and 37.7 wt %, respectively, was finally obtained.

Comparative Example 7

The reactions were carried out in the same manner as in Comparative Example except that isononanol was used instead of 2-ethylhexanol and that n-heptanol was used instead of n-butanol, and thereby a composition including tri(n-heptyl) trimellitate, di(n-heptyl)(isononyl) trimellitate, di(n-heptyl)isononyl trimellitate, and triisononyl trimellitate in an amount of 2.5 wt %, 12.0 wt %, 43.5 wt %, and 42.0 wt %, respectively, was finally obtained.

Comparative Example 8

The reactions were carried out in the same manner as in Example 1 except that esterification was carried out using 500 g of cyclohexane 1,2,4-tricarboxylic anhydride and 1,300 g of 2-ethylhexanol in the presence of a catalyst and that transesterification using n-butanol was not carried out, and thereby tri(2-ethylhexyl) cyclohexane 1,2,4-triester was obtained.

Comparative Example 9

The reactions were carried out in the same manner as in Comparative Example 8 except that 740 g of n-butanol was used instead of 2-ethylhexanol to carry out esterification in the presence of a catalyst, and thereby tri(n-butyl) cyclohexane 1,2,4-triester was obtained.

Comparative Example 10

The reactions were carried out in the same manner as in Comparative Example 8 except that 880 g of n-pentanol was used instead of 2-ethylhexanol to carry out esterification in the presence of a catalyst, and thereby triisopentyl cyclohexane 1,2,4-triester was obtained.

Comparative Example 11

The reactions were carried out in the same manner as in Comparative Example 8 except that 1,020 g of n-hexanol was used instead of 2-ethylhexanol to carry out esterification in the presence of a catalyst, and thereby tri(n-hexyl) cyclohexane 1,2,4-triester was obtained.

Comparative Example 12

By carrying out esterification in the presence of a catalyst using 1,020 g of n-hexanol instead of the 2-ethylhexanol used in Example 1 and then carrying out transesterification using butanol, a composition including tri(n-butyl) cyclohexane 1,2,4-triester, di(n-butyl)(n-hexyl) cyclohexane 1,2,4-triester, di(n-hexyl)(n-butyl) cyclohexane 1,2,4-triester, and tri(n-hexyl) cyclohexane 1,2,4-triester in an amount of 3.1 wt %, 13.8 wt %, 42.8 wt %, and 40.3 wt %, respectively, was finally obtained.

Comparative Example 13

By carrying out esterification in the presence of a catalyst using 1,440 g of isononanol instead of the 2-ethylhexanol used in Example 1 and then carrying out transesterification using n-heptanol, a composition including tri(n-heptyl) cyclohexane 1,2,4-triester, di(n-heptyl)isononyl cyclohexane 1,2,4-triester, di(isononyl)(n-heptyl) cyclohexane 1,2,4-triester, and triisononyl cyclohexane 1,2,4-triester in an amount of 2.7 wt %, 13.5 wt %, 45.1 wt %, and 38.7 wt %, respectively, was finally obtained.

Experimental Example 1: Evaluation of Sheet Performance

By using the plasticizers of Examples and Comparative Examples, test specimens were prepared in accordance with ASTM D638 with the following formulation and preparation conditions.

(1) Prescription: 100 parts by weight of a straight vinyl chloride polymer (LS100S), 40 parts by weight of a plasticizer, and 3 parts by weight of a stabilizer (BZ-153T)
(2) Mixing: performed at 98° C. and 700 rpm
(3) Test specimen preparation: The material was processed for 4 minutes using a roll mill at 160° C. and for 2.5 minutes (low pressure) and 2 minutes (high pressure) using a press at 180° C., and thereby 1T and 3T sheets were prepared.
(4) Test items
1) Hardness: In accordance with ASTM D2240, Shore hardness (Shore "A" and Shore "D") was measured at 25° C. for 10 seconds using a 3T test specimen. It is evaluated that smaller hardness values indicate better plasticization efficiency.

2) Tensile strength: In accordance with the method specified in ASTM D638, a 1T test specimen was pulled at a cross head speed of 200 mm/min using a UTM (4466 manufactured by Instron), and a time point at which the 1T test specimen was broken was determined. The tensile strength was calculated as follows:

Tensile strength (kgf/cm$^2$)=Load (kgf)/Thickness (cm)×Width (cm)

3) Elongation rate: In accordance with the method specified in ASTM D638, a 1T test specimen was pulled at a cross head speed of 200 mm/min using the UTM, and a time point at which the 1T test specimen was broken was determined. The elongation rate was calculated as follows:

Elongation rate(%)=Length after elongation/Initial length×100

4) Migration loss: In accordance with KSM-3156, a test specimen having a thickness of 2 mm or more was prepared, glass plates were attached to both sides of the 1T test specimen, and a load of 1 kgf/cm$^2$ was applied thereto. Subsequently, the test specimen was maintained in a hot-air convection oven (80° C.) for 72 hours and then taken out of the oven and cooled at room temperature for 4 hours. After removing the glass plates attached to both sides of the test specimen, the weights of the specimen plate before and after being maintained in the oven along with the glass plates were measured. The migration loss was calculated by the following equation:

Migration loss(%)={(Initial weight of test specimen at room temperature−Weight of test specimen after being maintained in oven)/Initial weight of test specimen at room temperature}×100

5) Volatile loss: The specimen prepared as described above was processed at 121° C. for 72 hours and then weighed, and the volatile loss was calculated by the following equation:

Volatile loss (wt %)=(Initial weight of test specimen−Weight of test specimen after being processed at 121° C. for 72 hours)/Initial weight of test specimen×100

6) Stress test (stress resistance): After maintaining a 2-mm-thick test specimen in a bent state at 23° C. for 1 day, 3 days, and 7 days, a degree of migration (i.e., a degree of bleeding) was evaluated, and the results were described numerically. In this case, values closer to 0 indicate better stress resistance.

7) Light resistance: In accordance with the method specified in ASTM 4329-13, the above-described test specimen was mounted on QUV (QUV/se manufactured by Q-LAB) and was exposed to UV irradiation (340 nm) for 200 hours or 400 hours, and a color change thereof was measured using a reflectometer (LoviBond manufactured by Tintometer GmbH).

(5) Evaluation results

The results of evaluating the above-described test items are shown in the following Table 1.

TABLE 1

| | Hardness | | Tensile strength (kgf/ cm$^2$) | Elongation rate (%) | Migration loss (%) | Volatile loss (%) |
|---|---|---|---|---|---|---|
| | (Shore A) | (Shore D) | | | | |
| Example 1 | 94.5 | 51.0 | 244.8 | 317.9 | 1.75 | 1.29 |
| Example 2 | 95.0 | 51.5 | 244.7 | 319.7 | 2.25 | 1.03 |
| Example 3 | 94.3 | 49.5 | 240.3 | 315.4 | 1.44 | 1.07 |
| Example 4 | 94.0 | 49.2 | 238.7 | 312.1 | 1.73 | 1.14 |
| Example 5 | 93.7 | 48.4 | 247.6 | 320.2 | 1.22 | 1.43 |
| Example 6 | 93.5 | 48.1 | 254.1 | 320.1 | 1.03 | 0.91 |
| Example 7 | 93.6 | 48.2 | 250.4 | 317.2 | 1.62 | 1.24 |
| Example 8 | 92.0 | 46.1 | 248.7 | 314.2 | 0.81 | 1.88 |
| Example 9 | 92.4 | 46.3 | 238.6 | 325.4 | 0.78 | 1.35 |
| Comparative Example 1 | 94.5 | 50.2 | 235.3 | 298.6 | 2.27 | 6.58 |
| Comparative Example 2 | 95.4 | 50.8 | 255.1 | 333.8 | 4.11 | 7.57 |
| Comparative Example 3 | 97.5 | 55.4 | 257.2 | 322.4 | 2.22 | 1.13 |
| Comparative Example 4 | 98.4 | 57.2 | 258.9 | 323.0 | 2.74 | 1.00 |
| Comparative Example 5 | 96.3 | 54.9 | 238.4 | 299.7 | 1.80 | 1.30 |
| Comparative Example 6 | 92.3 | 46.5 | 211.0 | 287.3 | 1.02 | 5.89 |
| Comparative Example 7 | 98.0 | 56.8 | 256.1 | 298.0 | 2.58 | 1.10 |
| Comparative Example 8 | 96.2 | 54.3 | 241.3 | 301.0 | 2.56 | 1.42 |
| Comparative Example 9 | — | — | — | — | — | — |
| Comparative Example 10 | 92.5 | 48.3 | 220.8 | 240.1 | 0.35 | 7.62 |
| Comparative Example 11 | 93.7 | 48.6 | 224.7 | 256.4 | 0.70 | 6.84 |
| Comparative Example 12 | 91.5 | 46.1 | 207.3 | 280.6 | 1.23 | 6.24 |
| Comparative Example 13 | 97.1 | 55.6 | 258.3 | 301.2 | 2.97 | 1.54 |

*Comparative Example 9: Unable to evaluate due to a very high absorption rate which made mixing impossible

TABLE 2

| | Stress resistance | | | Light resistance | |
|---|---|---|---|---|---|
| | 1 day | 3 days | 7 days | 200 hr | 400 hr |
| Example 1 | 0 | 0 | 0 | 1.01 | 1.35 |
| Example 2 | 0 | 0.5 | 0.5 | 1.23 | 1.32 |
| Example 3 | 0 | 0 | 0 | 1.44 | 1.46 |
| Example 4 | 0 | 0 | 0.5 | 1.49 | 1.48 |
| Example 5 | 0 | 0 | 0 | 1.35 | 1.40 |
| Example 6 | 0 | 0 | 0 | 1.38 | 1.42 |
| Example 7 | 0 | 0 | 0 | 1.20 | 1.32 |
| Example 8 | 0 | 0 | 0 | 1.02 | 1.11 |
| Example 9 | 0 | 0 | 0 | 1.23 | 1.25 |
| Comparative Example 1 | 0 | 0.5 | 1 | 0.82 | 1.02 |
| Comparative Example 2 | 0 | 2 | 2.5 | 3.82 | 10.29 |
| Comparative Example 3 | 0 | 0 | 0.5 | 3.44 | 7.06 |
| Comparative Example 4 | 0 | 0.5 | 1.5 | 4.36 | 12.03 |
| Comparative Example 5 | 0 | 0 | 0 | 3.06 | 5.89 |
| Comparative Example 6 | 0 | 0 | 0 | 4.50 | 9.86 |
| Comparative Example 7 | 0 | 0.5 | 1 | 4.22 | 8.76 |
| Comparative Example 8 | 0 | 1 | 1.5 | 1.25 | 1.50 |
| Comparative Example 9 | — | — | — | — | — |

TABLE 2-continued

| | Stress resistance | | | Light resistance | |
| --- | --- | --- | --- | --- | --- |
| | 1 day | 3 days | 7 days | 200 hr | 400 hr |
| Comparative Example 10 | 0 | 0 | 0 | 1.33 | 1.41 |
| Comparative Example 11 | 0 | 0 | 0 | 1.22 | 1.47 |
| Comparative Example 12 | 0 | 0 | 0 | 1.10 | 1.37 |
| Comparative Example 13 | 0 | 0.5 | 1 | 1.41 | 1.39 |

*Comparative Example 9: Unable to evaluate due to a very high absorption rate which made mixing impossible Referring to the results shown in Table 1 and Table 2, it can be confirmed that the plasticizers of Examples have uniformly excellent properties in terms of plasticization efficiency, tensile strength, an elongation rate, migration loss, and volatile loss as compared to the plasticizers of Comparative Examples, that considerably stable properties in terms of volatile loss characteristics and migration loss characteristics can be particularly secured, that a high level of plasticization efficiency, as well as high levels of tensile strength and elongation rate, can be ensured, and that particularly significant improvements have been made in terms of stress resistance and light resistance.

Specifically, in the case of Comparative Example 1, which is an existing product, it can be confirmed that most of its properties are inferior to those of Examples, and in the case of Comparative Example 2, which is an improvement (DEHTP) on the product of Comparative Example 1, although some properties have been improved, since migration loss characteristics and volatile loss characteristics have been degraded rather than improved, it can be confirmed that the properties thereof are also inferior to those of the plasticizers of Examples.

In addition, the trimellitates of Comparative Examples 3 and 4 show superiority in some other physical properties, but have high hardness and thus are confirmed to have very poor plasticization efficiency. Furthermore, although the trimellitates of Comparative Example 3 and 4 may not be a type of product that has environmental issues, the potential for the trimellitates of Comparative Example 3 and 4 to cause such issues due to having a benzene ring therein cannot be ruled out. Therefore, considering the above-described characteristics and the fact that the trimellitates of Comparative Example 3 and 4 have excellent mechanical properties but poor plasticization efficiency, it is predicted that the trimellitates of Comparative Example 3 and 4 will have a very low industrial advantage as compared with the plasticizers of Examples.

The above prediction can also be applied to the plasticizers of Comparative Examples 5 to 7, which are trimellitate-based plasticizers like Comparative Examples 3 and 4.

In addition, it can also be seen that it may be difficult to improve properties through hydrogenation unless the carbon numbers of lower alkyls and higher alkyls are properly controlled in the plasticizer composition according to one exemplary embodiment of the present invention. As a result of comparing Comparative Example 5 with Example 1 in which the carbon numbers of lower alkyls and higher alkyls have been properly controlled, it can be seen that plasticization efficiency and light resistance can be greatly improved through hydrogenation and that it is possible to also improve tensile strength and an elongation rate while allowing other properties to be maintained at an equivalent level or improved.

However, hydrogenation may reduce rather than improve tensile strength and elongation when the carbon numbers have not been controlled, as can be seen by comparing Comparative Examples 3 and 8, Comparative Examples 6 and 12, and Comparative Examples 7 and 13.

In addition, as can be seen from Comparative Examples 9 to 11, in the case of hydrogenated non-hybrid-type trimellitates to which only lower alkyls have been applied, very poor properties are exhibited in terms of tensile strength, an elongation rate, and volatile loss, and in the case of Comparative Example 4, mixing was impossible due to a very high absorption rate. In addition, it can also be seen that even if the compounds are modified into a hybrid form, the above-described characteristics cannot be overcome as long as the selection of alkyls is made only from among lower alkyls.

Meanwhile, it can be seen that when a hybrid-type compound is formed using only higher alkyls, low plasticization efficiency is exhibited, and even though the weight has been increased, elongation is degraded rather than improved because the alkyls are imbalanced.

The invention claimed is:

1. A cyclohexane triester-based plasticizer composition comprising each of:

a lower non-hybrid-type cyclohexane triester including a compound of Chemical Formula 1;

a lower hybrid-type cyclohexane triester including two or more compounds of Chemical Formula 2;

a higher hybrid-type cyclohexane triester including two or more compounds of Chemical Formula 3; and a higher non-hybrid-type cyclohexane triester including a compound of Chemical Formula 4, Chemical Formula 1
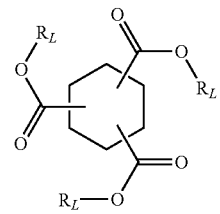

Chemical Formula 2
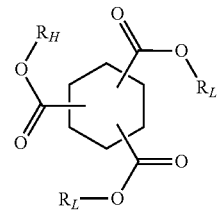

Chemical Formula 3
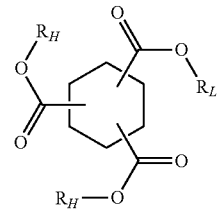

-continued

Chemical Formula 4

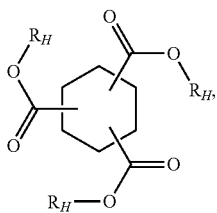

wherein in Chemical Formulas 1 to 4, $R_L$ is a C3-C6 alkyl group, and $R_H$ is a C7-C10 alkyl group.

2. The plasticizer composition of claim 1, wherein the compound of Chemical Formula 1 is represented by Chemical Formula 1a, and the compound of Chemical Formula 4 is represented by Chemical Formula 4a:

Chemical Formula 1a

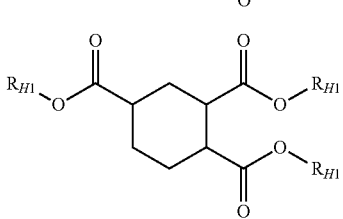

Chemical Formula 4a

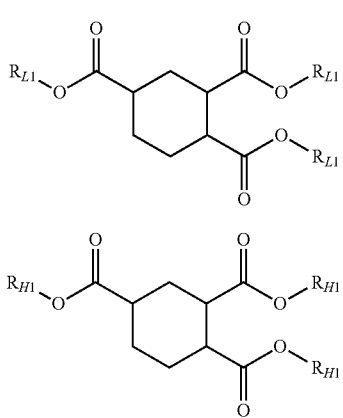

wherein, in Chemical Formulas 1a and 4a, $R_{L1}$ is a C3-C6 alkyl group, and $R_{H1}$ is a C7-C10 alkyl group.

3. The plasticizer composition of claim 1,
wherein the two or more compounds of Chemical Formula 2 comprises each of:
a lower hybrid ortho-type cyclohexane triester of Chemical Formula 2a;
a lower hybrid meta-type cyclohexane triester of Chemical Formula 2b; and
a lower hybrid para-type cyclohexane triester of Chemical Formula 2c:

Chemical Formula 2a

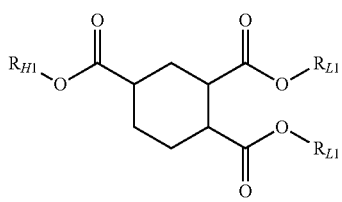

Chemical Formula 2b

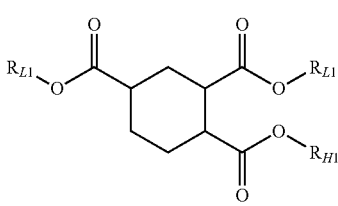

Chemical Formula 2c

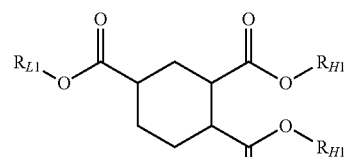

wherein the two or more compounds of Chemical Formula 3 comprises each of:
a higher hybrid ortho-type cyclohexane triester of Chemical Formula 3a;
a higher hybrid meta-type cyclohexane triester of Chemical Formula 3b; and
a higher hybrid para-type cyclohexane triester of Chemical Formula 3c:

Chemical Formula 3a

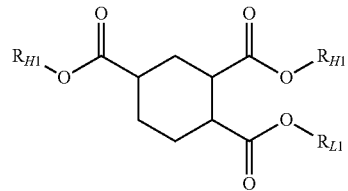

Chemical Formula 3b

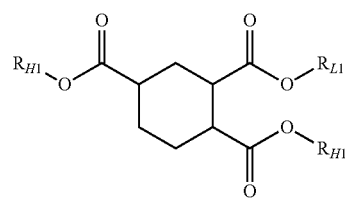

Chemical Formula 3c

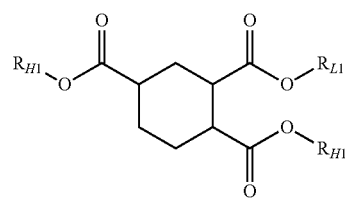

wherein in Chemical Formulas 2a to 2c and Chemical Formulas 3a to 3c, $R_{L1}$ is a C3-C6 alkyl group, and $R_{H1}$ is a C7-C10 alkyl group.

4. The plasticizer composition of claim 1, wherein in Chemical Formulas 1 to 4, $R_L$ is a C4-C6 alkyl group, and $R_H$ is a C8-C10 alkyl group.

5. The plasticizer composition of claim 1, wherein in Chemical Formulas 1 to 4, $R_L$ is a C5 or C6 alkyl group, and $R_H$ is a C8 or C9 alkyl group.

6. The plasticizer composition of claim 1, comprising:
the lower non-hybrid-type cyclohexane triester in an amount of 0.01 wt % to 70 wt %,
the lower hybrid-type cyclohexane triester in an amount of 5 wt % to 70 wt %,
the higher hybrid-type cyclohexane triester in an amount of 5 wt % to 70 wt %, and
the higher non-hybrid-type cyclohexane triester in an amount of 0.01 wt % to 70 wt %.

7. The plasticizer composition of claim 1, comprising:
the lower non-hybrid-type cyclohexane triester in an amount of 0.5 wt % to 50 wt %, the lower hybrid-type cyclohexane triester in an amount of 10 wt % to 50 wt %, the higher hybrid-type cyclohexane triester in an amount of 10 wt % to 50 wt %, and the higher non-hybrid-type cyclohexane triester in an amount of 0.5 wt % to 50 wt %.

8. The plasticizer composition of claim 1, wherein in Chemical Formulas 1 to 4, $R_L$ is selected from the group consisting of a butyl group, an isobutyl group, an n-pentyl group, an isopentyl group, an n-hexyl group, and an isohexyl group;

$R_H$ is selected from the group consisting of an n-heptyl group, an isoheptyl group, an n-octyl group, an isooctyl group, a 2-ethylhexyl group, an n-nonyl group, an isononyl group, an n-decyl group, an isodecyl group, and a 2-propylheptyl group, and wherein each of the isobutyl group, the isopentyl group, the isohexyl group, the isoheptyl group, the isooctyl group, the isononyl group, and the isodecyl group refers to an alkyl group having a methyl group or ethyl group as a branched chain.

9. The plasticizer composition of claim 1, wherein in Chemical Formulas 1 to 4, $R_L$ is selected from the group consisting of an n-pentyl group, an isopentyl group, an n-hexyl group, and an isohexyl group;

$R_H$ is selected from the group consisting of a 2-ethylhexyl group, an isononyl group, an isodecyl group, and a 2-propylheptyl group, and wherein each of the isopentyl group, the isohexyl group, the isononyl group, and the isodecyl group refers to an alkyl group having a methyl group or ethyl group as a branched chain.

10. A resin composition comprising:

a resin in an amount of 100 parts by weight; and the plasticizer composition of claim 1 in an amount of 5 parts by weight to 150 parts by weight.

11. The resin composition of claim 10, wherein the resin is one or more selected from the group consisting of a straight vinyl chloride polymer, a paste vinyl chloride polymer, an ethylene vinyl acetate copolymer, an ethylene polymer, a propylene polymer, a polyketone, a polystyrene, a polyurethane, a natural rubber, a synthetic rubber, and a thermoplastic elastomer.

* * * * *